United States Patent [19]
Clare et al.

[11] Patent Number: 5,718,719
[45] Date of Patent: Feb. 17, 1998

[54] SWITCH APPARATUS AND METHOD FOR SWITCHING BETWEEN MULTIPLE ELECTRODES FOR DIAGNOSTIC AND THERAPEUTIC PROCEDURES

[75] Inventors: Christopher R. Clare, Los Altos Hills; Mir A. Imran, Palo Alto, both of Calif.

[73] Assignee: Physiometrix, Inc., N. Billerica, Mass.

[21] Appl. No.: 686,021

[22] Filed: Jul. 25, 1996

Related U.S. Application Data

[63] Continuation of Ser. No. 243,229, May 16, 1994, Pat. No. 5,540,722.
[51] Int. Cl.⁶ ................................................. A61N 1/39
[52] U.S. Cl. ................................................. 607/5
[58] Field of Search ................................ 607/5; 128/696

[56] References Cited

U.S. PATENT DOCUMENTS

| 4,852,585 | 8/1989 | Heath | 128/798 |
| 4,895,169 | 1/1990 | Heath | 128/798 |

Primary Examiner—William E. Kamm

[57] ABSTRACT

A switch apparatus for performing diagnostic and/or therapeutic procedures on a patient by the use of first and second electrodes which are placed on a patient. A defibrillator unit and another medical device utilizing radio frequency energy from a radio frequency generator unit comprises a multifunction adapter unit. The adapter unit is coupled to the first and second electrodes, to the defibrillator unit and to the electrosurgery unit for switching between the defibrillation unit and another medical device to permit performing diagnostic and therapeutic procedures on the patient.

15 Claims, 4 Drawing Sheets

SWITCH APPARATUS AND METHOD FOR SWITCHING BETWEEN MULTIPLE ELECTRODES FOR DIAGNOSTIC AND THERAPEUTIC PROCEDURES

This is a continuation of application Ser. No. 08/243,229 filed May 16, 1994, now U.S. Pat. No. 5,540,722.

This invention relates to a switch apparatus and method for switching between multiple electrodes for diagnostic and therapeutic procedures, and more particularly to such an apparatus and method which can be performed with only two electrodes.

In many medical procedures, particularly those involving the heart, a defibrillator is generally connected directly to the patient by the use of self-adhesive defibrillation pads. In addition, in surgical procedures being performed on a patient utilizing radio frequency for electrocautery or ablation, there is a need to attach one or more additional radio frequency return pads to the patient, typically to the thigh or leg. In such procedures, there is normally no connection between the RF return electrodes and the defibrillation electrodes. In other words, the defibrillation system and the electrosurgery or ablation systems are independent of each other. Thus, a patient for a single surgical procedure may require the use of four large-area electrodes for performing two separate functions. In order to reduce the expense of surgical procedures, there is a need to reduce the number of pads required for surgical procedures. There is therefore a need for the switch apparatus and method which can be utilized for switching between multiple electrodes for performing diagnostic and therapeutic procedures.

In general, it is an object of the present invention to provide a switch apparatus and method for switching between medical multiple electrodes for diagnostic and therapeutic procedures.

Another object of the invention is to provide an apparatus and method of the above character which only requires the use of two electrodes.

Another object of the invention is to provide an apparatus and method of the above character which prevents errors from improperly connecting electrodes.

Another object of the invention is to provide an apparatus and method which utilizes separate adapter and indicator units.

Another object of the invention is to provide an apparatus and method of the above character which only requires a single cable from an indicator unit to the adapter unit.

Another object of the invention is to provide an apparatus and method of the above character which automatically switches between defibrillation and RF return functions for the electrodes.

Another object of the invention is to provide an apparatus and method of the above character which reduces costs and the time needed in performing medical procedures.

Additional objects and features of the invention will appear from the following description in which the preferred embodiment is set forth in detail in conjunction with the accompanying drawings.

Figure 1:
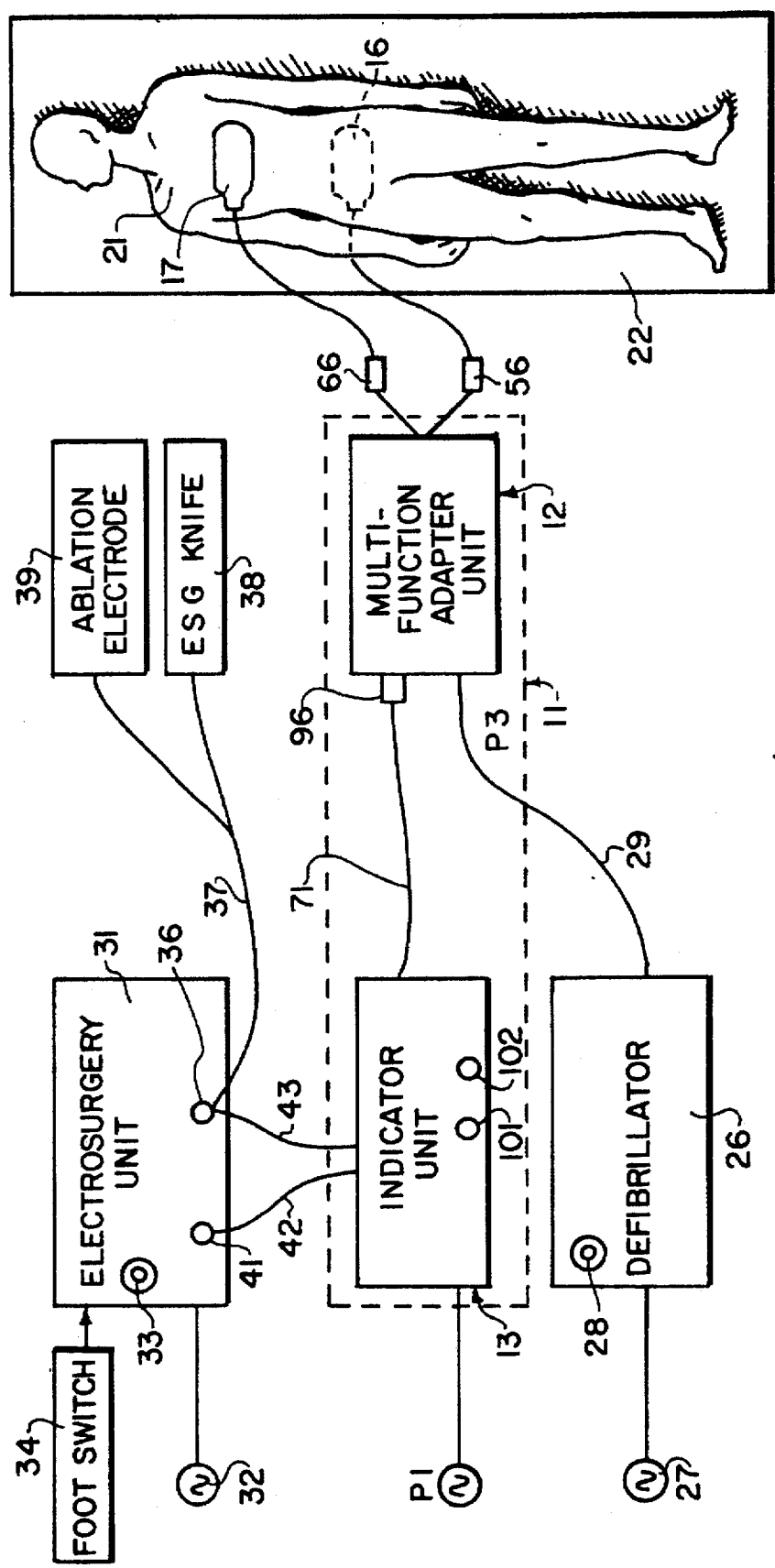
FIG. 1 is a block diagram of a switch apparatus incorporating the present invention.
Figure 2:
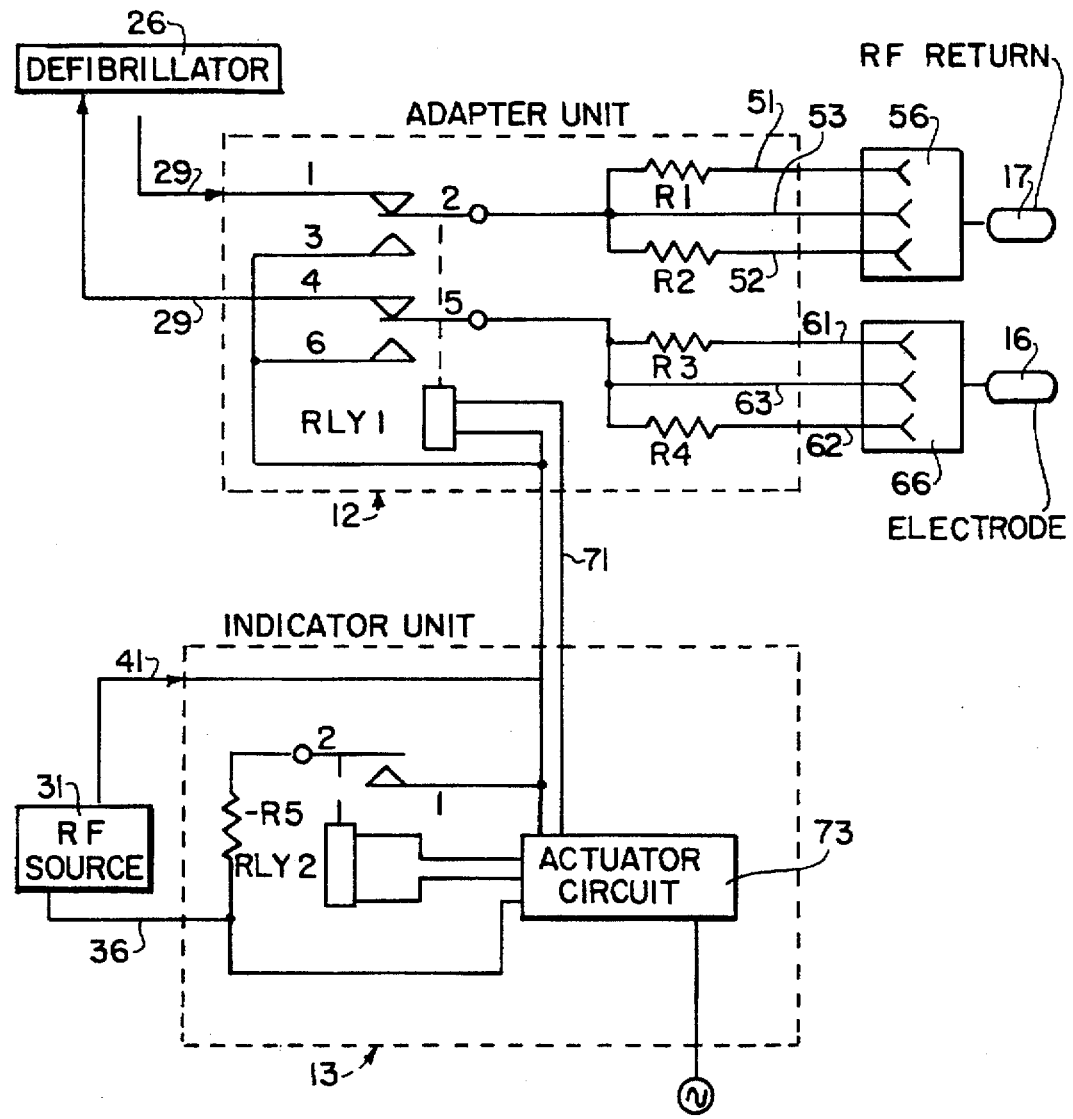
FIG. 2 is a block diagram of the adapter unit and the indicator unit utilized in the switch apparatus in FIG. 1.

In general, the switch apparatus for performing diagnostic and therapeutic procedures on a patient utilizing a defibrillating unit and an electrosurgery unit and first and second electrodes adapted to be placed on the patient comprises a multi-function adapter adapted to be coupled to the first and second electrodes, and adapted to the coupled to the defibrillator unit and to the electrosurgery unit for switching between the defibrillation unit and the electrosurgery unit to permit performing procedures on the patient utilizing the same first and second electrodes.

More particularly, as shown in FIGS. 1–4 of the drawings, the switch apparatus 11 consists of a multi-function adapter unit 12 and an indicator unit 13. The switch apparatus 11 is adapted to be connected to first and second electrodes 16 and 17 which can be of a large surface area electrode of the type described in U.S. Pat. No. 5,295,482. The electrodes 16 and 17 are adapted to be placed in contact with the skin of a patient 21 lying on a table 22. The switch apparatus 11 is adapted to be used with other types of medical apparatus, as for example a defibrillator 26 as shown in block form which is connected to the source 27 of conventional 110 volt 60 cycle AC power. It is provided with an ON-OFF switch 28 and a cable 29 which is connected to the switch apparatus 11 as hereinafter described.

The switch apparatus 11 is also adapted to be connected to another medical device such as an electrosurgery unit 31 of a conventional type, which is also shown in block form and also is connected to a conventional source 32 of 110 60 cycle volt AC power. It is provided with an ON-OFF button 33. It is also provided with a foot switch 34 to control the application of radio frequency energy from an outlet receptacle 36 that is connected by a cable 37 to an electrosurgical (ESG) knife 38. Alternatively, cable 37 can be connected to an ablation electrode 39. It is also provided with a return receptacle 41, which is connected by a cable 42 to the switch apparatus 11 as hereinafter described. Similarly, the RF connector 36 is also connected by cable 43 to the switch apparatus 11 by a cable 43.

The multi-function adapter unit 12 includes a vacuum relay identified as RLY-1 (see FIG. 2) which is rated for high voltage and high current. It should be able to withstand high currents from the defibrillator 26 and provide greater than 10,000 volt isolation between the defibrillator 26 and the RF supply 31 so that the electrosurgery unit 31 is protected from damage from high voltage defibrillation pulses. It also prevents patient shock. The relay RLY-1 can be of a suitable type such as manufactured by Kilovac of Santa Barbara, Calif.

The relay RLY-1 is provided with stationary contacts 1, 3, 4 and 6, and movable contacts 2 and 5. The stationary contacts 1 and 4 are connected to the + and − terminals of the defibrillation 26 by conductors in a cable 29. The movable contact 2 of the relay RLY-1 is connected to two resistors, R1 and R2, which are connected in parallel to leads 51 and 52 and directly to a lead 53, all of which are connected into a connector 56 that is adapted to be connected to the RF return electrode 17 that, as described in U.S. Pat. No. 5,295,482, can be provided with three segments with substantially uniform current flow from the segments into the skin of the patient 21. Similarly, the movable contact 5 of the relay RLY-1 is connected to resistors R3 and R4 connected in parallel to leads 61, 62 and directly to a lead 63, all of which are connected into a connector 66 that is adapted to be connected to the electrode 16 in a similar manner in which the connector 56 is connected to the electrode 17.

Figure 3:
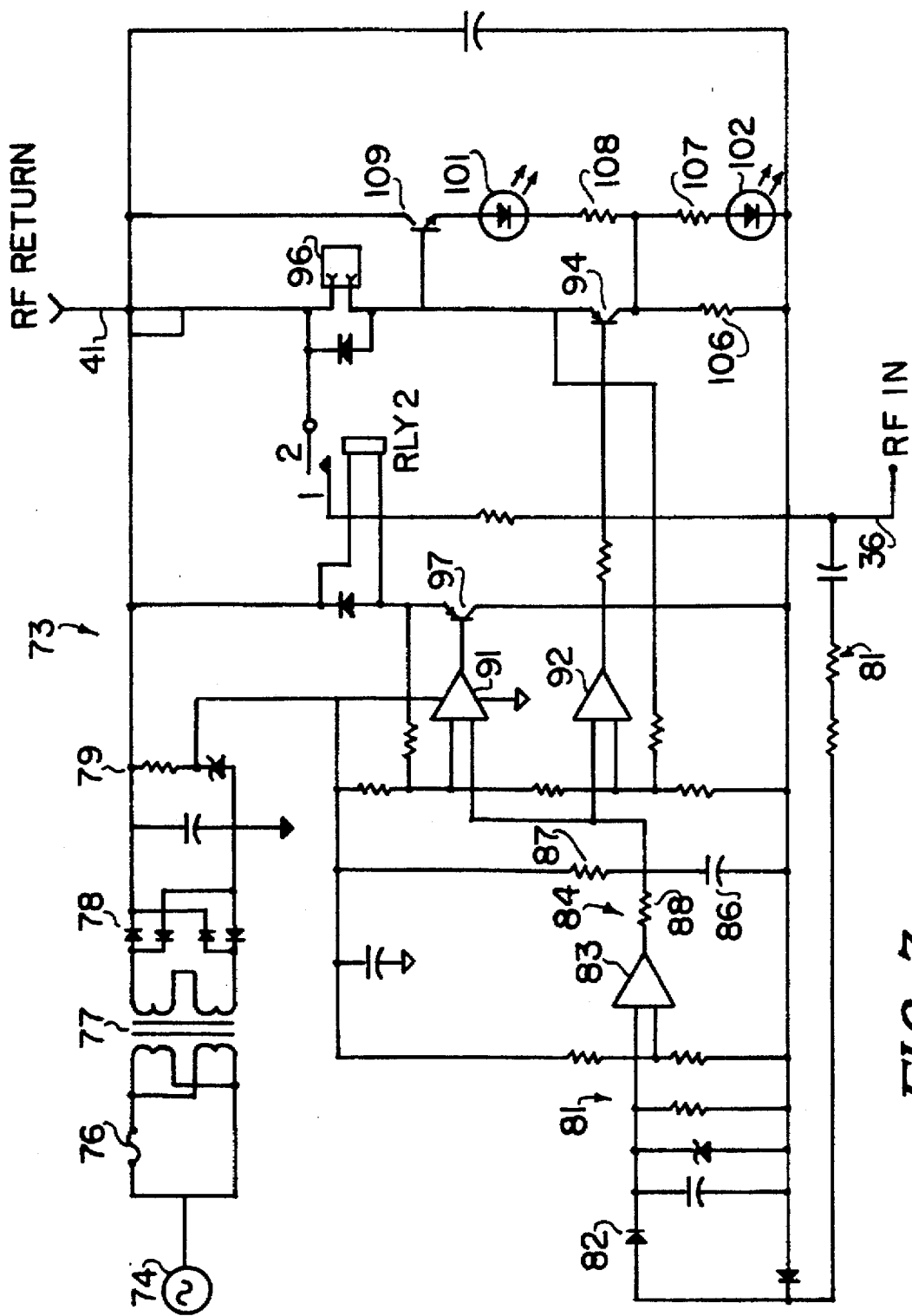
FIG. 3 is a circuit diagram of the electrical circuit utilized in the indicator unit shown in FIG. 2.

The relay RLY-1 is actuated from a high-voltage relay signal supplied on a signal cable 71 interconnecting the adapter unit 12 to the indicator unit 13. The indicator unit 13 is provided with an actuator circuit 73 into which the cable 71 is connected. The actuator circuit 73 is provided with power from a conventional AC power source 74, such as 110 volts, 60 cycle AC. The actuator circuit 73 which is shown in FIG. 3 and hereinafter described in detail is provided with means for detecting the presence of radio frequency energy coming in from an external source to the switch apparatus 11. The external source in this case is the radio frequency generated by the electrosurgery unit 31, which is provided with the RF output conductor 36 and a return conductor 41. As soon as the actuator circuit 73 detects that radio frequency energy is present, the relay RLY-1 is operated to move the movable contacts 2 and 5 out of engagement with the stationary contacts 1 and 4 connected to the defibrillator 26.

The actuator circuit 73 also operates a relay RLY-2 which is provided with a stationary contact 1 and a movable contact 2 with the stationary contact 1 being connected to the return side of the RF source 31 and the other movable contact 2 being connected through a termination resistor R5 and thence back to the RF source 31. The termination resistor R5 supplies a radio frequency dummy load to the RF source 31 during the time that the defibrillation relay RLY-1 is switching from the supply from the defibrillator 26 to the supply from the radio frequency source 31. This dummy load provided by the resistor R5 serves to prevent the radio frequency source 31 from believing it is not connected to anything at any point in time and thereby prevents the radio frequency source from shutting itself off which it normally would do if it detected an open circuit.

The actuator circuit 73 is shown in detail in FIG. 3 as AC power supply 74 is connected through a fuse 76 to a transformer 77 the output of which is connected to a diode array 78 through a filter network 79 to provide a DC voltage for operating the relay RLY-1. Line voltage is isolated from the patient by a double-insulated transformer 77. The transformer output is rectified and filtered to provide a source of 24 volts DC. The DC voltage generated within the indicator unit is isolated from the radio frequency circuit by capacitors. The radio frequency input 36 is supplied through a serial capacitative resistive network 81 to a detector 82 that generates a DC voltage proportional to the received radio frequency signal which is compared with a reference provided on an input comparator 83. When the voltage to the comparator 83 is greater than the threshold voltage provided by the reference, an output is supplied by the comparator 83 to start a timing circuit in the form of an RC network 84 consisting of a capacitor 86 and a resistor 87, so the voltage across the capacitor 86 increases exponentially with time. The output from the network 84 is supplied to threshold detectors 91 and 92, both of which are provided with references. When the value from the timing circuit 84 increases above the threshold for the comparator 92, a signal is supplied by the comparator 92 to turn on a transistor 94 which supplies power to a connector 96 through the cable 71 to energize relay RLY-1 to switch the adapter unit 12 from a defibrillation function to a radio frequency energy function. The relay RLY-2 will remain energized until the output level from the timing circuit 84 reaches a value which is above the threshold value for the comparator 91. It then supplies an input to the transistor 97 to remove power from the relay RLY-2 to disconnect the dummy load provided by the resistor R5 from the radio frequency supply 36.

Thus it can be seen that as soon as radio frequency energy is applied to the actuator circuit 73, the actuator circuit 73 detects the presence of radio frequency energy and provides a small time delay as determined by the RC network 84 to ensure that radio frequency is present, after which adapter unit relay RLY-1 is energized. Then after another time delay allowing the adapter relay RLY-1 to close, the relay RLY-1 that switches the adapter unit 12 from a defibrillation function to a radiofrequency function and the second relay RLY-2 is denergized to disconnect the load provided by the resistor R5 from the radio frequency supply 36.

Thus it can be seen that the circuitry shown in FIG. 3 makes it possible to automatically switch between defibrillation and RF return functions for the RF electrode 16. This makes it possible to share the RF return electrode with two separate functions, as for example defibrillation and radio frequency energy uses such as electrocautery and ablation. This makes it possible to provide both diagnostic and therapeutic procedures on a patient utilizing as few as two electrodes.

As hereinbefore described, one electrode 17 would be placed on the back of the patient and the electrode 16 would be placed on the apex of the heart of the patient. Thus, in making the connection to the defibrillator 26, one electrode is tied to the "plus" side of the defibrillator whereas the other electrode is connected to the "minus" side of the defibrillator. During an RF return procedure, the relay RLY-1 in the adapter unit 12 is connected to both the defibrillation electrodes 16 and 17 and to the RF return so that current is connected through both whereby an even larger surface area of the skin of the patient is provided for RF return to thereby minimize any possible burning. In addition, the reliability of the connection to the patient is enhanced.

Thus, the switch apparatus hereinbefore described makes it possible to eliminate the use of one electrode by sharing the two remaining electrodes to perform the same function. In addition to the cost saving for the electrodes. The switch apparatus also reduces the labor required to perform a surgical procedure since one less electrode need be placed on the body of the patient and needs to be removed after the surgical procedure has been completed.

In order to give a physical indication of the operation of the relays RLY-1 and RLY-2, indication means in the form of light emitting diodes 101 and 102 are provided to respectively provide a green color and a yellow color. The diode 102 (yellow) is energized when the transistor 94 is triggered and when the relay RLY-1 is energized. The LED 101 (green) is energized through a transistor 109 when the adapter unit is properly connected to the indicator unit and RF is not present and the indicator unit is turned on.

Figure 4:
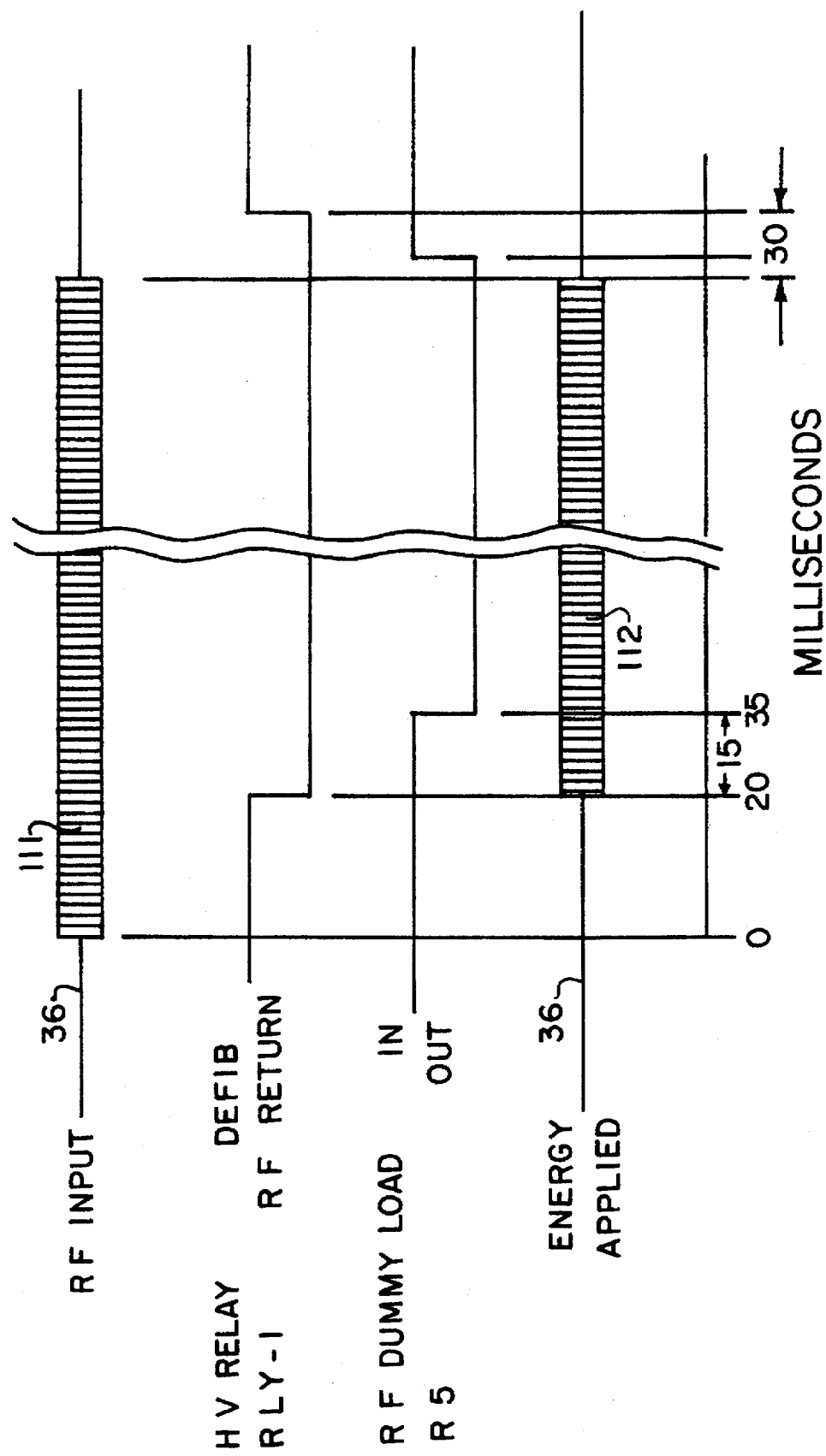
FIG. 4 is a timing diagram of the method utilized in the present invention.

A timing diagram for the timing utilized in the circuitry shown in FIG. 3 is shown in FIG. 4. Thus, as soon as radio frequency energy is applied as represented by the waveform 111, there is a time delay ranging from 10 to 20 milliseconds before the high voltage relay RLY-1 is energized to ensure that a transient radio frequency signal has not been received. The dummy load R5 is maintained on the radio frequency energy source 31 for an additional period of time ranging from 10 to 20 milliseconds, and by way of example, 15 ms as shown, to provide a 15-ms overlap as represented by the waveform 112 to supply energy.

When radio frequency energy is turned off, this is sensed by the comparator 83 which rapidly discharges the capacitor 86 through the resistor 88 within a fairly short time constant to cause the radio frequency load to be applied to the RF generator 31 and shortly thereafter causing the energy to be removed from the relay RLY-1 to cause the adapter unit 12 to switch back to the defibrillation mode.

The chart set forth below shows eight possible combinations which can occur when it is desired to ascertain whether or not the switch apparatus 11 is connected to an AC outlet, whether or not the cable is connected between the indicator unit 13 and the multi-function adapter unit 12 and whether or not the RF power is turned on or off.

| AC Power | Connection to Adapter | RF Power | Lights | Adapter Function |
|---|---|---|---|---|
| ON | YES | OFF | Green | Defibrillation |
| ON | YES | ON | Yellow | RF Return |
| ON | NO | OFF | None | Defibrillation |
| ON | NO | ON | None | Defibrillation; RF generator will detect an open circuit |
| OFF | YES | OFF | None | Defibrillation |
| OFF | YES | ON | None | Defibrillation; RF generator will detect an open circuit |
| OFF | NO | OFF | None | Defibrillation |
| OFF | NO | ON | None | Defibrillation; RF generator will detect an open circuit |

From the chart above, it can be seen that the AC power is turned on and the connections are made to the adapter and the RF is off, the light emitting diode 101 will be energized to provide a green color to indicate that the switch apparatus 11 is in the defibrillation mode and that it is functioning properly. All energy will be supplied to the patient in the event that defibrillation is desired. The next line of the chart with the RF power on, the yellow light emitting diode will be energized which indicates that the RF return is connected properly to the patient or that the radio frequency energy will be returned to the radio frequency generator. Thereafter, there are listed six fault conditions in the chart. Thus, if the AC power is on but there is no connection to the adapter unit 12, neither of the LEDs 101, 102 will be energized. Similarly, other fault conditions are set forth in the chart which are evident from the legends given in the chart. Thus it can be seen that the only time that the green light comes on is when everything is connected properly. In the event of a fault being generated, the switch apparatus 11 will always default to a defibrillation mode so that the patient is protected. The yellow light would only be lit when the radio frequency energy is returned and the AC power is turned on and the connection is proper to the adapter unit and the radio frequency is turned on.

One of the principal features of the invention is that only two wires in the cable 71 are required for connection between the adapter unit 12 and the indicator unit 13. One of these wires is used for the RF return and the other wire is to power the relay RLY-1. The same wire that carries the RF return is shared for power in the relay. In addition, those two wires are used to detect whether or not the adapter unit is plugged into the multi-function cable adapter. This is accomplished as hereinbefore described by having one of the wires to the cable adapter being tied to the RF return and also to the positive supply of the indicator unit which is floating from the power line and everything else because of the isolation provided by transformer 77. The other wire of the cable 71 to the adapter unit 12 connected to circuitry which includes a transistor 94 which turns on the voltage to the relay RLY-1 and to the resistors 106, 107 and 108 and the two LEDs 101 and 102 and the transistor 109 which act as detectors on the connections to the adapter unit 12.

By way of example, when the cable 71 is plugged into the adapter unit 12, the transistor 94 off, meaning that the relay RLY-1 is not actuated, a small amount of current will flow through the high voltage relay RLY-1 which small amount of current is sufficient to turn on the transistor 109 which will energize the green LED 101. However, this current is insufficient to energize the high voltage relay RLY-1. If the cable 71 is disconnected, the green light 101 will not be turned on. When the cable 71 is connected, the transistor 94 shorts out the voltage across the resistor 108 and the LED 101 causing it to turn off and at the same time causing current to flow through the voltage relay RLY-1 to cause it to be energized. The current flowing through the high voltage relay RLY-1 and flowing through the transistor 94 also flows through the resistor 106 causing a voltage drop which is sufficient to cause current to flow through the resistor R107 to energize the yellow LED 102. Unless a current flows through the resistor 107 of a sufficient magnitude, the yellow LED 102 will not be energized. A current can then only flow through the resistor 106 through the cable 71 and back through the RF return, so that if the cable is removed, the yellow light will not light. Thus it can be seen that the interlock circuitry provided in FIG. 3 is directly related to the connection to the high voltage relay RLY-1. All of these functions which are set forth in the chart above and are accomplished through the two wires in cable 71 between the adapter unit 12 and the indicator unit 13 in a failsafe manner, so that at all times it is known whether or not the cable is connected.

From the foregoing it can be seen that there has been provided a switch apparatus which makes it possible to switch between two electrodes automatically and to do it safely in a fail safe manner so that nothing is damaged during the time that switching is occurring. The switch apparatus will always failsafe to the defibrillator function. So far as the doctor or physician operating on the patient, the doctor can operate the ablation electrode or the ESG knife 38 of the switch apparatus just as though there were separate sets of electrodes for each therapeutic and diagnostic function performed by him. The switch apparatus 11 makes it possible for the doctor to perform a defibrillation whenever desired, and to also apply radio frequency energy when desired.

What is claimed is:

1. A switch apparatus for performing diagnostic and/or therapeutic procedures on a patient by the use of first and second electrodes adapted to be placed on the patient and by the use of a defibrillator unit and another medical device utilizing radio frequency energy from a radio frequency generator unit comprising a multi-function adapter unit adapted to be coupled to the first and second electrodes and adapted to be coupled to the defibrillator unit and another electrical device for switching between the defibrillation unit and said another medical device to permit performing the diagnostic and therapeutic procedures on the patient utilizing the same first and second electrodes.

2. A switch apparatus in claim 1 wherein said multi-function adapter unit includes means for using both of said first and second electrodes as return electrodes when performing a procedure using said another medical device.

3. A switch apparatus as in claim 1 wherein said multi-function adapter unit includes means for sensing when radio frequency energy from the radiofrequency generator unit is present.

4. A switch apparatus as in claim 1 wherein said multi-function adapter unit includes relay means for switching between the defibrillator unit and the another surgical device.

5. A switch apparatus as in claim 4 wherein said multi-function adapter unit includes an actuator circuit for sensing the presence or absence of radio frequency energy from the radio frequency generator unit, means connected to the actuator circuit for supplying a radio frequency dummy load to the radio frequency generator unit when the relay means is being switched from the defibrillator unit to the another medical device to ensure that the actuator circuit will not sense at any time the absence of an RF signal.

6. A switch apparatus as in claim 4 together with an indicator unit coupled to the multi-function adapter unit, said indicator unit having first and second light means, means for energizing the first light means when the defibrillator unit is being used and means for energizing the second light means when the another medical device is being used.

7. A switch apparatus as in claim 6 further comprising first and second conductors and wherein said indicator unit is connected to said multi-function adapter unit solely by said first and second conductors.

8. A switch apparatus as in claim 6 wherein said indicator unit includes additional relay means connected to the actuator circuit for ascertaining when radio frequency energy is being supplied to the actuator circuit, said additional relay means including means for supplying a dummy load to the radio frequency generator unit during the time that the first relay is operated.

9. A switch apparatus as in claim 8 wherein the multi-function adapter unit includes a plurality of resistors adapted to be coupled to the first and second electrodes to help to establish a substantially uniform current distribution from the electrodes into the patient.

10. A switch apparatus as in claim 8 wherein said indicator unit includes means for connecting the electrodes to the defibrillator whenever radio frequency energy is not being used.

11. A switch apparatus as in claim 8 wherein said indicator unit includes failsafe means for detecting a fault condition and for connecting the electrodes to the defibrillator unit when a fault condition occurs.

12. A method for performing diagnostic and therapeutic procedures on a patient with first and second electrodes adapted to be placed on the body of the patient and a defibrillator unit and another medical device utilizing radio frequency energy from a radio frequency generator unit comprising connecting the another medical device to the first and second electrodes, ascertaining the absence of radio frequency energy from the radio frequency generator unit and connecting the first and second electrodes to the defibrillator unit when the absent radio frequency energy is sensed and at the same time disconnecting the electrodes from the another medical device.

13. A method as in claim 12 together with the step of sensing a fault condition and connecting the first and second electrodes to the defibrillator when the fault condition is sensed.

14. A method as in claim 12 together with the step of connecting a radio frequency dummy load to the radio frequency generator unit when switching from the defibrillator unit to the another medical device.

15. A method as in claim 12 together with the step of utilizing the same first and second electrodes for use of the defibrillator unit and for use of the another medical device.

* * * * *